(12) United States Patent
Fruchey et al.

(10) Patent No.: US 8,937,147 B2
(45) Date of Patent: *Jan. 20, 2015

(54) PROCESSES FOR PRODUCING DIAMINOBUTANE (DAB), SUCCINIC DINITRILE (SDN) AND SUCCINAMIDE (DAM)

(76) Inventors: Olan S. Fruchey, Hurricane, WV (US);
Leo E. Manzer, Wilmington, DE (US);
Dilum Dunuwila, Princeton, NJ (US);
Brian T. Keen, Pinch, WV (US); Brooke A. Albin, Charleston, WV (US); Nye A. Clinton, Hurricane, WV (US); Bernard D. Dombek, Charleston, WV (US)

( * ) Notice: Subject to any disclaimer, the term of this patent is extended or adjusted under 35 U.S.C. 154(b) by 39 days.

This patent is subject to a terminal disclaimer.

(21) Appl. No.: 13/697,633

(22) PCT Filed: May 18, 2011

(86) PCT No.: PCT/US2011/036913
§ 371 (c)(1),
(2), (4) Date: Jan. 16, 2013

(87) PCT Pub. No.: WO2011/146556
PCT Pub. Date: Nov. 24, 2011

(65) Prior Publication Data
US 2013/0172519 A1     Jul. 4, 2013

Related U.S. Application Data

(60) Provisional application No. 61/346,145, filed on May 19, 2010.

(51) Int. Cl.
*C08G 69/26* (2006.01)
*C08G 63/44* (2006.01)
*C07C 239/00* (2006.01)
*C07C 209/00* (2006.01)
*C07C 253/00* (2006.01)
*C07C 209/46* (2006.01)
*C07C 51/44* (2006.01)
*C07C 209/48* (2006.01)
*C07C 231/02* (2006.01)
*C07C 253/20* (2006.01)
*C07C 253/22* (2006.01)
*C07C 253/30* (2006.01)

(52) U.S. Cl.
CPC ............. *C07C 209/46* (2013.01); *C07C 51/445* (2013.01); *C07C 209/48* (2013.01); *C07C 231/02* (2013.01); *C07C 253/20* (2013.01); *C07C 253/22* (2013.01); *C07C 253/30* (2013.01); *C08G 69/26* (2013.01)
USPC ........... 528/335; 564/138; 564/468; 564/491; 564/490; 528/362; 558/311; 558/459

(58) Field of Classification Search
USPC .......... 528/335, 362; 564/468, 138, 491, 490; 558/459, 311
See application file for complete search history.

(56) References Cited

U.S. PATENT DOCUMENTS

| 2,166,971 | A | * | 7/1939 | Schmidt et al. | 564/468 |
|---|---|---|---|---|---|
| 2,223,303 | A | | 11/1940 | Lazier | |
| 3,296,303 | A | | 1/1967 | Nemec et al. | |
| 3,579,583 | A | | 5/1971 | Rutzen et al. | |
| 4,003,933 | A | | 1/1977 | Drake | |
| 4,237,067 | A | | 12/1980 | Küster et al. | |
| 4,935,546 | A | | 6/1990 | Barrault et al. | |
| 4,990,550 | A | * | 2/1991 | Iwanami et al. | 523/214 |
| 5,109,104 | A | | 4/1992 | Marks | |
| 5,151,543 | A | | 9/1992 | Ziemecki | |
| 5,587,498 | A | | 12/1996 | Krogh et al. | |
| 6,376,714 | B1 | * | 4/2002 | Allgeier et al. | 564/492 |
| 6,958,381 | B2 | * | 10/2005 | Winterling et al. | 528/322 |
| 7,132,562 | B2 | | 11/2006 | Allgeier | |
| 2007/0161813 | A1 | * | 7/2007 | Meudt et al. | 558/382 |
| 2013/0144028 | A1 | * | 6/2013 | Fruchey et al. | 528/335 |

FOREIGN PATENT DOCUMENTS

| JP | 05-097776 | * | 4/1993 |
|---|---|---|---|
| JP | 09-208539 | * | 8/1997 |
| JP | 11-029538 | * | 2/1999 |
| JP | 2005-139156 | * | 6/2005 |
| JP | 2007-254354 | * | 10/2007 |
| JP | 2007 254354 | | 10/2007 |

OTHER PUBLICATIONS

Translation of JP2007-254354.*
Translation of JP09-208539.*
Translation of JP2005-139156.*
Translation of JP11-029538.*
Translation of JP05-097776.*
Jacobi et al., "Dihydropyrromethenones by Pd(0)-Mediated Coupling of Iodopyrroles and Acetylenic Amides. Synthesis of the A,B Ring Segment of Phytochrome," J. Org. Chem. 62, 2907-2916, 1997.*
Datsenko, K.A. et al., "One-Step Inactivation of Chromosomal Genes in *Escherichia coli* K-12 Using PCR Products," Proc. Natl. Acad. Sci. U S A, Jun. 6, 2000, vol. 97, No. 12, pp. 6640-6645 (Abstract only—2 sheets).
Bochner, B.R. et al., "Positive Selection for Loss of Tetracycline Resistance," *Journal of Bacteriology*, Aug. 1980, vol. 143, No. 2, pp. 926-933.

* cited by examiner

*Primary Examiner* — Paul A Zucker
*Assistant Examiner* — Mark Luderer
(74) *Attorney, Agent, or Firm* — Paula DeGrandis

(57) ABSTRACT

Processes that make nitrogen-containing compounds include converting succinic acid (SA) or monoammonium succinate (MAS) derived from a diammonium succinate (DAS)- or MAS-containing fermentation broth to produce such compounds including diaminobutane (DAB), succinic dinitrile (SDN), succinic amino nitrile (SAN), succinamide (DAM), and related polymers.

19 Claims, 4 Drawing Sheets

FIG. 2   MAS to SAN, SDN, DAB, DAM and Polyamides

FIG. 3   SA to SAN, SDN, DAM, DAB and Polyamides

PROCESSES FOR PRODUCING DIAMINOBUTANE (DAB), SUCCINIC DINITRILE (SDN) AND SUCCINAMIDE (DAM)

RELATED APPLICATIONS

This is a §371 of International Application No. PCT/US2011/036913, with an international filing date of May 18, 2011 (WO 2011/146556 A1, published Nov. 24, 2011), which is based on U.S. Patent Application No. 61/346,145 filed May 19, 2010, the subject matter of which is incorporated herein by reference.

TECHNICAL FIELD

This disclosure relates to processes for producing nitrogen containing compounds such as DAB, SDN and DAM from succinic acid (SA) and monoammonium succinate (MAS) produced by fermentation.

BACKGROUND

Certain carbonaceous products of sugar fermentation are seen as replacements for petroleum-derived materials for use as feedstocks for the manufacture of carbon-containing chemicals. One such product is MAS.

A material related to MAS, namely SA, can be produced by microorganisms using fermentable carbon sources such as sugars as starting materials. However, most commercially viable, succinate producing microorganisms described in the literature neutralize the fermentation broth to maintain an appropriate pH for maximum growth, conversion and productivity. Typically, the pH of the fermentation broth is maintained at or near a pH of 7 by introduction of ammonium hydroxide into the broth, thereby converting the SA to diammonium succinate (DAS). The DAS may be converted to MAS to derive MAS from the fermentation broth.

Kushiki (Japanese Published Patent Application, Publication No. 2005-139156) discloses a method of obtaining MAS from an aqueous solution of DAS that could be obtained from a fermentation broth to which an ammonium salt is added as a counter ion. Specifically, MAS is crystallized from an aqueous solution of DAS by adding acetic acid to the solution to adjust the pH of the solution to a value between 4.6 and 6.3, causing impure MAS to crystallize from the solution.

Masuda (Japanese Unexamined Application Publication P2007-254354, Oct. 4, 2007) describes partial deammoniation of dilute aqueous solutions of "ammonium succinate" of the formula $H_4NOOCCH_2CH_2COONH_4$. From the molecular formula disclosed, it can be seen that "ammonium succinate" is diammonium succinate. Masuda removes water and ammonia by heating solutions of the ammonium succinate to yield a solid SA-based composition containing, in addition to ammonium succinate, at least one of MAS, SA, monoamide succinate, succinimide, succinamide or ester succinate. Thus, it can be inferred that like Kushiki, Masuda discloses a process that results in production of impure MAS. The processes of both Kushiki and Masuda lead to materials that need to be subjected to various purification regimes to produce high purity MAS.

Bio-derived MAS and SA such as that derived from MAS itself are platform molecules for synthesis of a number of commercially important chemicals and polymers. Therefore, it is highly desirable to provide a purification technology that offers flexibility to integrate clear, commercially viable paths to derivatives such as DAB, SDN and DAM. In response to the lack of an economically and technically viable process solution for converting fermentation-derived SA/MAS to DAB, SDN, succinic amino nitrile (SAN) and DAM, it could be helpful to provide methods for providing a cost effective SA/MAS stream of sufficient purity for direct hydrogenation.

SUMMARY

We provide a process for making nitrogen containing compounds of SA, including (a) providing a clarified DAS-containing fermentation broth; (b) distilling the broth to form an overhead that comprises water and ammonia, and a liquid bottoms that comprises MAS, at least some DAS, and at least about 20 wt % water; (c) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS; (d) separating at least part of the solid portion from the liquid portion; and (e) (1) contacting the solid portion with hydrogen and optionally an ammonia source in the presence of at least one hydrogenation catalyst to produce DAB; or (2) dehydrating at least a part of the solid portion to produce SDN; or (3) dehydrating at least a part of the solid portion to produce DAM; and (f) recovering the DAB, SDN or DAM.

We also provide a process for making nitrogen containing compounds of SA, including (a) providing a clarified DAS-containing fermentation broth; (b) distilling the broth to form a first overhead that includes water and ammonia, and a first liquid bottoms that includes MAS, at least some DAS, and at least about 20 wt % water; (c) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS; (d) separating the solid portion from the liquid portion; (e) recovering the solid portion; (f) dissolving the solid portion in water to produce an aqueous MAS solution; (g) distilling the aqueous MAS solution at a temperature and pressure sufficient to form a second overhead that includes water and ammonia, and a second bottoms that includes a major portion of SA, a minor portion of MAS, and water; (h) cooling and/or evaporating the second bottoms to cause the second bottoms to separate into a second liquid portion in contact with a second solid portion that preferably consists essentially of SA and is substantially free of MAS; (i) separating at least part of the second solid portion from the second liquid portion; and (j) (1) contacting the second solid portion with hydrogen and an ammonia source in the presence of at least one hydrogenation catalyst to produce DAB; or (2) dehydrating at least a part of the second solid portion to produce SDN; or (3) dehydrating at least a part of the second solid portion to produce DAM; and (k) recovering the DAB, SDN or DAM.

We further provide a process for making nitrogen containing compounds, including (a) providing a clarified MAS-containing fermentation broth; (b) optionally, adding MAS, DAS, SA, $NH_3$, and/or $NH_4^+$ to the broth to preferably maintain the pH of the broth below 6; (c) distilling the broth to form an overhead that includes water and optionally ammonia, and a liquid bottoms that includes MAS, at least some DAS, and at least about 20 wt % water; (d) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS; (e) separating at least part of the solid portion from the liquid portion; and (f) (1) contacting the solid portion with hydrogen and optionally an ammonia source in the presence of at least one hydrogenation catalyst to produce DAB; or (2) dehydrating at least a part of the second solid portion to produce SDN; or (3) dehydrating at least a part of the second solid portion to produce DAM; and (g) recovering the DAB, SDN or DAM.

We further yet provide a process for making nitrogen containing compounds, including (a) providing a clarified MAS-containing fermentation broth; (b) optionally, adding MAS, DAS, SA, $NH_3$, and/or $NH_4^+$ to the broth to preferably maintain the pH of the broth below 6; (c) distilling the broth to form an overhead that includes water and optionally ammonia, and a liquid bottoms that includes MAS, at least some DAS, and at least about 20 wt % water; (d) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS; (e) separating the solid portion from the liquid portion; and (f) recovering the solid portion; (g) dissolving the solid portion in water to produce an aqueous MAS solution; (h) distilling the aqueous MAS solution at a temperature and pressure sufficient to form a second overhead that includes water and ammonia, and a second bottoms that includes a major portion of SA, a minor portion of MAS, and water; (i) cooling and/or evaporating the second bottoms to cause the second bottoms to separate into a second liquid portion in contact with a second solid portion that preferably consists essentially of SA and is substantially free of MAS; (j) separating at least part of the second solid portion from the second liquid portion; and (k) (1) contacting the solid portion with hydrogen and an ammonia source in the presence of at least one hydrogenation catalyst to produce DAB; or (2) dehydrating at least a part of the solid portion to produce SDN; or (3) dehydrating at least a part of the solid portion to produce DAM; and (1) recovering the DAB, SDN or DAM.

DETAILED DESCRIPTION

Figure 1:
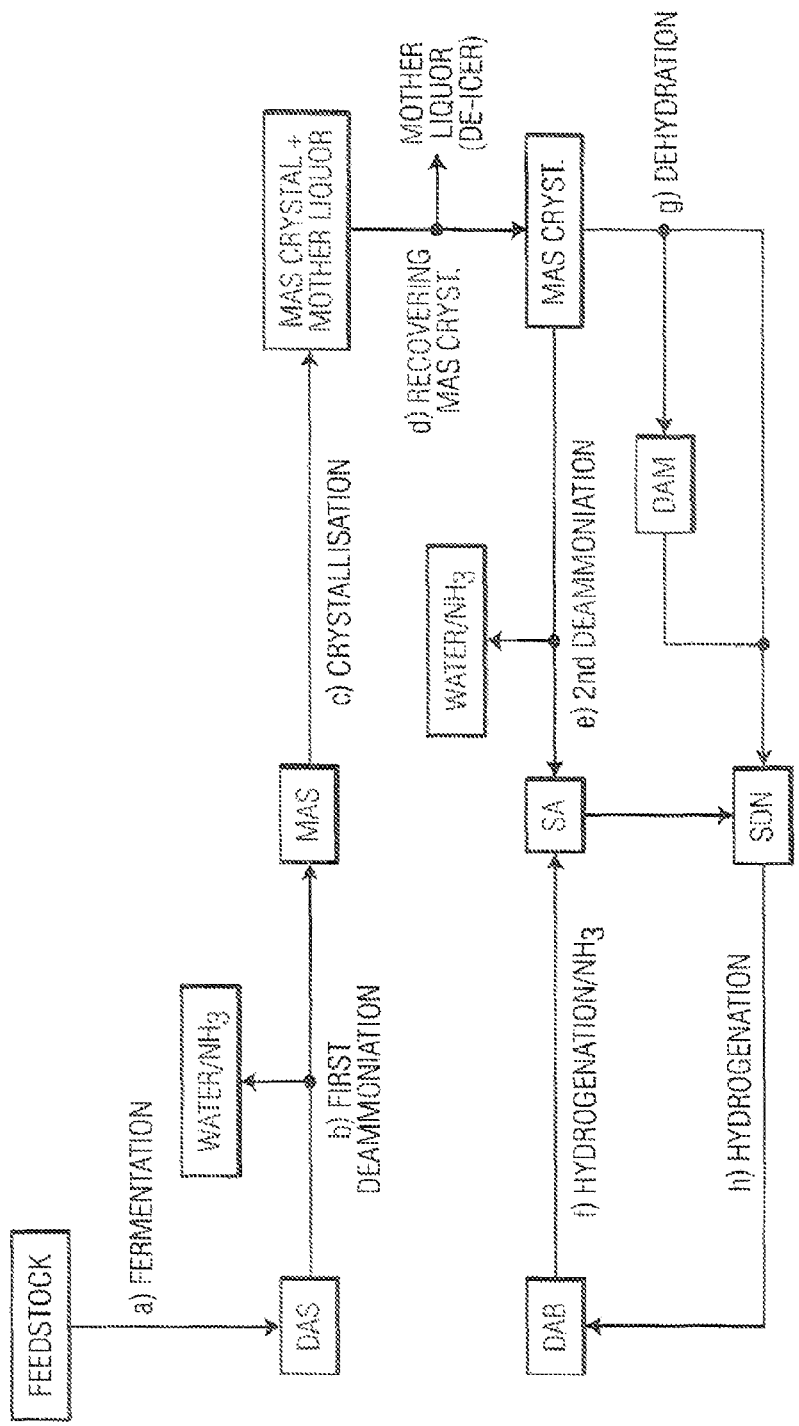
FIG. 1 schematically illustrates a fully integrated process for producing fermentation-derived SA/MAS and further converting SA/MAS to DAB and SDN and depicts two-stage deammoniation of DAS with a MAS crystallization step between the two stages.

It will be appreciated that at least a portion of the following description is intended to refer to representative examples of processes selected for illustration in the drawings and is not intended to define or limit the disclosure, other than in the appended claims.

Our processes may be appreciated by reference to FIG. 1, which shows in flow diagram form one representative example of our methods.

A growth vessel, typically an in-place steam sterilizable fermentor, may be used to grow a microbial culture (not shown) that is subsequently utilized for the production of the DAS, MAS, and/or SA-containing fermentation broth. Such growth vessels are known in the art and are not further discussed.

The microbial culture may comprise microorganisms capable of producing SAs from fermentable carbon sources such as carbohydrate sugars. Representative examples of microorganisms include, *Escherichia coli* (*E. coli*), *Aspergillus niger*, *Corynebacterium glutamicum* (also called *Brevibacterium flavum*), *Enterococcus faecalis*, *Veillonella parvula*, *Actinobacillus succinogenes*, *Mannheimia succiniciproducens*, *Anaerobiospirillum succiniciproducens*, *Paecilomyces Varioti*, *Saccharomyces cerevisiae*, *Bacteroides fragilis*, *Bacteroides ruminicola*, *Bacteroides amylophilus*, *Alcaligenes eutrophus*, *Brevibacterium ammoniagenes*, *Brevibacterium lactofermentum*, *Candida brumptii*, *Candida catenulate*, *Candida mycoderma*, *Candida zeylanoides*, *Candida paludigena*, *Candida sonorensis*, *Candida utilis*, *Candida zeylanoides*, *Debaryomyces hansenii*, *Fusarium oxysporum*, *Humicola lanuginosa*, *Kloeckera apiculata*, *Kluyveromyces lactis*, *Kluyveromyces wickerhamii*, *Penicillium simplicissimum*, *Pichia anomala*, *Pichia besseyi*, *Pichia media*, *Pichia guilliermondii*, *Pichia inositovora*, *Pichia stipidis*, *Saccharomyces bayanus*, *Schizosaccharomyces pombe*, *Torulopsis candida*, *Yarrowia lipolytica*, mixtures thereof and the like.

A preferred microorganism is an *E. coli* strain deposited at the ATCC under accession number PTA-5132. More preferred is this strain with its three antibiotic resistance genes (cat, amphl, tetA) removed. Removal of the antibiotic resistance genes cat (coding for the resistance to chloramphenicol), and amphl (coding for the resistance to kanamycin) can be performed by the so-called "Lambda-red (λ-red)" procedure as described in Datsenko K A and Wanner B L., Proc. Natl. Acad. Sci. USA 2000 Jun. 6; 97(12) 6640-5, the subject matter of which is incorporated herein by reference. The tetracycline resistant gene tetA can be removed using the procedure originally described by Bochner et al., J. Bacteriol. 1980 August; 143(2): 926-933, the subject matter of which is incorporated herein by reference. Glucose is a preferred fermentable carbon source for this microorganism.

A fermentable carbon source (e.g., carbohydrates and sugars), optionally a source of nitrogen and complex nutrients (e.g., corn steep liquor), additional media components such as vitamins, salts and other materials that can improve cellular growth and/or product formation, and water may be fed to the growth vessel for growth and sustenance of the microbial culture. Typically, the microbial culture is grown under aerobic conditions provided by sparging an oxygen-rich gas (e.g., air or the like). Typically, an acid (e.g., sulphuric acid or the like) and ammonium hydroxide are provided for pH control during the growth of the microbial culture.

In one example (not shown), the aerobic conditions in the growth vessel (provided by sparging an oxygen-rich gas) are switched to anaerobic conditions by changing the oxygen-rich gas to an oxygen-deficient gas (e.g., $CO_2$ or the like). The anaerobic environment triggers bioconversion of the fermentable carbon source to SA in situ in the growth vessel. Ammonium hydroxide is provided for pH control during bioconversion of the fermentable carbon source to SA. The SA that is produced is at least partially neutralized to DAS due to the presence of the ammonium hydroxide, leading to the production of a broth comprising DAS. The $CO_2$ provides an additional source of carbon for the production of SA.

In another example, the contents of the growth vessel may be transferred via a stream to a separate bioconversion vessel for bioconversion of a carbohydrate source to SA. An oxygen-deficient gas (e.g., $CO_2$ or the like) is sparged in the bioconversion vessel to provide anaerobic conditions that trigger production of SA. Ammonium hydroxide is provided for pH control during bioconversion of the carbohydrate source to SA. Due to the presence of the ammonium hydroxide, the SA produced is at least partially neutralized to DAS, leading to production of a broth that comprises DAS. The $CO_2$ provides an additional source of carbon for production of SA.

In another example, the bioconversion may be conducted at relatively low pH (e.g., 3 to 6). A base (ammonium hydroxide or ammonia) may be provided for pH control during bioconversion of the carbohydrate source to SA. Depending of the desired pH, due to the presence or lack of the ammonium hydroxide, either SA is produced or the SA produced is at least partially neutralized to MAS, DAS, or a mixture comprising SA, MAS and/or DAS. Thus, the SA produced during bioconversion can be subsequently neutralized, optionally in an additional step, by providing either ammonia or ammonium hydroxide leading to a broth comprising DAS. As a consequence, a "DAS-containing fermentation broth" generally means that the fermentation broth comprises DAS and possibly any number of other components such as MAS and/or SA, whether added and/or produced by bioconversion or otherwise. Similarly, a "MAS-containing fermentation broth" generally means that the fermentation broth comprises MAS and possibly any number of other components such as DAS and/or SA, whether added and/or produced by bioconversion or otherwise.

The broth resulting from the bioconversion of the fermentable carbon source (in either the growth vessel or the bioconversion vessel, depending on where the bioconversion takes place), typically contains insoluble solids such as cellular biomass and other suspended material, which are transferred via a stream to a clarification apparatus before distillation. Removal of insoluble solids clarifies the broth. This reduces or prevents fouling of subsequent distillation equipment. The insoluble solids can be removed by any one of several solid-liquid separation techniques, alone or in combination, including but not limited to, centrifugation and filtration (including, but not limited to ultra-filtration, micro-filtration or depth filtration). The choice of filtration can be made using techniques known in the art. Soluble inorganic compounds can be removed by any number of known methods such as, but not limited to, ion-exchange, physical adsorption and the like.

An example of centrifugation is a continuous disc stack centrifuge. It may be useful to add a polishing filtration step following centrifugation such as dead-end or cross-flow filtration that may include the use of a filter aide such as diatomaceous earth or the like, or more preferably ultra-filtration or micro-filtration. The ultra-filtration or micro-filtration membrane can be ceramic or polymeric, for example. One example of a polymeric membrane is SelRO MPS-U20P (pH stable ultra-filtration membrane) manufactured by Koch Membrane Systems (850 Main Street, Wilmington, Mass., USA). This is a commercially available polyethersulfone membrane with a 25,000 Dalton molecular weight cut-off which typically operates at pressures of 0.35 to 1.38 MPa (maximum pressure of 1.55 MPa) and at temperatures up to 50° C. Alternatively, a filtration step may be employed, such as ultra-filtration or micro-filtration alone.

The resulting clarified DAS-containing broth or MAS-containing broth, substantially free of the microbial culture and other solids, is transferred via a stream to a distillation apparatus.

The clarified distillation broth should contain DAS and/or MAS in an amount that is at least a majority of, preferably at least about 70 wt %, more preferably 80 wt % and most preferably at least about 90 wt % of all the diammonium dicarboxylate salts in the broth. The concentration of DAS and/or MAS as a weight percent (wt %) of the total dicarboxylic acid salts in the fermentation broth can be easily determined by high pressure liquid chromatography (HPLC) or other known means.

Water and ammonia are removed from the distillation apparatus as an overhead, and at least a portion is optionally recycled via a stream to the bioconversion vessel (or the growth vessel operated in the anaerobic mode). Distillation temperature and pressure are not critical as long as the distillation is carried out in a way that ensures that the distillation overhead contains water and ammonia, and the distillation bottoms comprises at least some DAS and at least about 20 wt % water. A more preferred amount of water is at least about 30 wt % and an even more preferred amount is at least about 40 wt %. The rate of ammonia removal from the distillation step increases with increasing temperature and also can be increased by injecting steam (not shown) during distillation. The rate of ammonia removal during distillation may also be increased by conducting distillation under a vacuum or by sparging the distillation apparatus with a non-reactive gas such as air, nitrogen or the like.

Removal of water during the distillation step can be enhanced by the use of an organic azeotroping agent such as toluene, xylene, cyclohexane, methyl cyclohexane, methyl isobutyl ketone, heptane or the like, provided that the bottoms contains at least about 20 wt % water. If the distillation is carried out in the presence of an organic agent capable of forming an azeotrope consisting of the water and the agent, distillation produces a biphasic bottoms that comprises an aqueous phase and an organic phase, in which case the aqueous phase can be separated from the organic phase, and the aqueous phase used as the distillation bottoms. Byproducts such as succinamic acid, succinamide and succinimide are substantially avoided provided the water level in the bottoms is maintained at a level of at least about 30 wt %.

A preferred temperature for the distillation step is in the range of about 50° C. to about 300° C., depending on the pressure. A more preferred temperature range is about 90° C. to about 150° C., depending on the pressure. A distillation temperature of about 110° C. to about 140° C. is preferred. "Distillation temperature" refers to the temperature of the bottoms (for batch distillations this may be the temperature at the time when the last desired amount of overhead is taken).

Adding a water miscible organic solvent or an ammonia separating solvent facilitates deammoniation over a variety of distillation temperatures and pressures as discussed above. Such solvents include aprotic, bipolar, oxygen-containing solvents that may be able to form passive hydrogen bonds. Examples include, but are not limited to, diglyme, triglyme, tetraglyme, propylene glycol, sulfoxides such as dimethylsulfoxide (DMSO), lactones such as gamma-butyrolactonce (GBL), amides such as dimethylformamide (DMF) and dimethylacetamide, sulfones such as dimethylsulfone, sulfolane, polyethyleneglycol (PEG), butoxytriglycol, N-methylpyrolidone (NMP), ethers such as dioxane, methyl ethyl ketone (MEK) and the like. Such solvents aid in the removal of ammonia from the DAS or MAS in the clarified broth. Regardless of the distillation technique, it is important that the distillation be carried out in a way that ensures that at least some DAS and at least about 20 wt % water remain in the bottoms and even more advantageously at least about 30 wt %.

The distillation can be performed at atmospheric, sub-atmospheric or super-atmospheric pressures. The distillation can be a one-stage flash, a multistage distillation (i.e., a multistage column distillation) or the like. The one-stage flash can be conducted in any type of flasher (e.g., a wiped film evaporator, thin film evaporator, thermosiphon flasher, forced circulation flasher and the like). The multistages of the distillation column can be achieved by using trays, packing or the like. The packing can be random packing (e.g., Raschig rings, Pall rings, Berl saddles and the like) or structured packing (e.g., Koch-Sulzer packing, Intalox packing, Mellapak and the like). The trays can be of any design (e.g., sieve trays, valve trays, bubble-cap trays and the like). The distillation can be performed with any number of theoretical stages.

If the distillation apparatus is a column, the configuration is not particularly critical, and the column can be designed using well known criteria. The column can be operated in either stripping mode, rectifying mode or fractionation mode. Distillation can be conducted in either batch or continuous mode. In the continuous mode, the broth is fed continuously into the distillation apparatus, and the overhead and bottoms are continuously removed from the apparatus as they are formed. The distillate from distillation is an ammonia/water solution, and the distillation bottoms is a liquid, aqueous solution of MAS and DAS, which may also contain other fermentation by-product salts (i.e., ammonium acetate, ammonium formate, ammonium lactate and the like) and color bodies.

The distillation bottoms can be transferred via a stream to a cooling apparatus and cooled by conventional techniques. Cooling technique is not critical. A heat exchanger (with heat recovery) can be used. A flash vaporization cooler can be used to cool the bottoms to about 15° C. Cooling to <15° C. typically employs a refrigerated coolant such as, for example, glycol solution or, less preferably, brine. A concentration step can be included prior to cooling to help increase product yield. Further, both concentration and cooling can be combined using methods known such as vacuum evaporation and heat removal using integrated cooling jackets and/or external heat exchangers.

Figure 4:
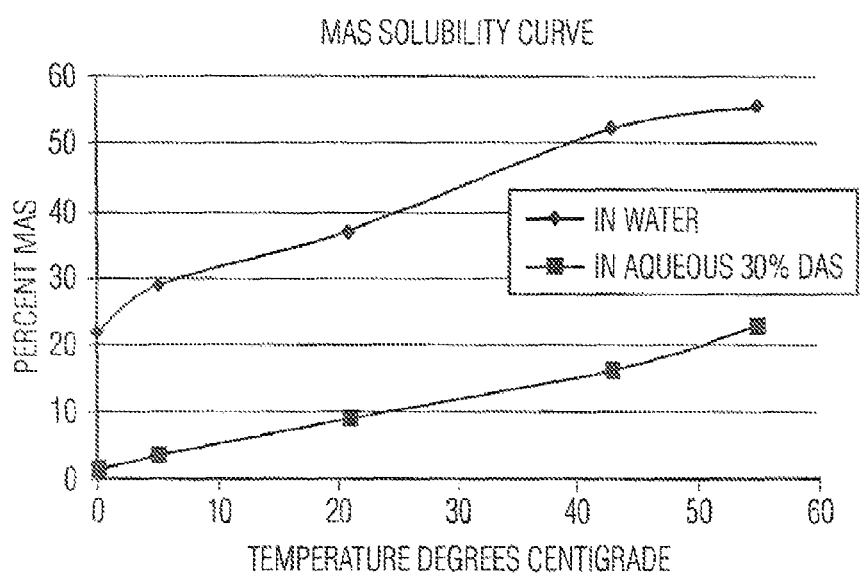
FIG. 4 is a graph showing the solubility of MAS as a function of temperature in both water and a 30% aqueous DAS solution.

We found that the presence of some DAS in the liquid bottoms facilitates cooling-induced separation of the bottoms into a liquid portion in contact with a solid portion that at least "consists essentially" of MAS (meaning that the solid portion is at least substantially pure crystalline MAS) by reducing the solubility of MAS in the liquid, aqueous, DAS-containing bottoms. FIG. 4 illustrates the reduced solubility of MAS in an aqueous 30 wt % DAS solution at various temperatures ranging from 0° C. to 60° C. The upper curve shows that even at 0° C. MAS remains significantly soluble in water (i.e., about 20 wt % in aqueous solution). The lower curve shows that at 0° C. MAS is essentially insoluble in a 30 wt % aqueous DAS solution. We discovered, therefore, that MAS can be more completely crystallized out of an aqueous solution if some DAS is also present in that solution. A preferred concentration of DAS in such a solution is in the ppm to about 3 wt % range. This allows crystallization of MAS (i.e., formation of the solid portion of the distillation bottoms) at temperatures higher than those that would be required in the absence of DAS.

When about 50% of the ammonia is removed from DAS contained in an aqueous medium the succinate species establish an equilibrium molar distribution that is about 0.1:0.8:0.1 in DAS:MAS:SA within a pH range of 4.8 to 5.4, depending on the operating temperature and pressure. When this composition is concentrated and cooled, MAS exceeds its solubility limit in water and crystallizes. When MAS undergoes a phase change to the solid phase, the liquid phase equilibrium resets thereby producing more MAS (DAS donates an ammonium ion to SA). This causes more MAS to crystallize from solution and continues until appreciable quantities of SA are exhausted and the pH tends to rise. As the pH rises, the liquid phase distribution favors DAS. However, since DAS is highly soluble in water, MAS continues to crystallize as its solubility is lower than DAS. In effect, the liquid phase equilibrium and the liquid-solid equilibria of succinate species act as a "pump" for MAS crystallization, thereby enabling MAS crystallization in high yield.

In addition to cooling, evaporation, or evaporative cooling described above, crystallization of MAS can be enabled and/or facilitated by addition of an antisolvent. In this context, antisolvents may be solvents typically miscible with water, but cause crystallization of a water soluble salt such as MAS due to lower solubility of the salt in the solvent. Solvents with an antisolvent effect on MAS can be alcohols such as ethanol and propanol, ketones such as methyl ethyl ketone, ethers such as tetrahydrofuran and the like. The use of antisolvents is known and can be used in combination with cooling and evaporation or separately.

The distillation bottoms, after cooling in the cooling unit, is fed via a stream to a separator for separation of the solid portion from the liquid portion. Separation can be accomplished via pressure filtration (e.g., using Nutsche or Rosenmond type pressure filters), centrifugation and the like. The resulting solid product can be recovered as a product and dried, if desired, by standard methods.

After separation, it may be desirable to treat the solid portion to ensure that no liquid portion remains on the surface(s) of the solid portion. One way to minimize the amount of liquid portion that remains on the surface of the solid portion is to wash the separated solid portion with water and dry the resulting washed solid portion. A convenient way to wash the solid portion is to use a so-called "basket centrifuge." Suitable basket centrifuges are available from The Western States Machine Company (Hamilton, Ohio, USA).

The liquid portion of the distillation bottoms (i.e., the mother liquor) may contain remaining dissolved MAS, any unconverted DAS, any fermentation byproducts such as ammonium acetate, lactate, or formate, and other minor impurities. This liquid portion can be fed via a stream to a downstream apparatus. In one instance, the downstream apparatus may be a means for making a de-icer by treating in the mixture with an appropriate amount of potassium hydroxide, for example, to convert the ammonium salts to potassium salts. Ammonia generated in this reaction can be recovered for reuse in the bioconversion vessel (or the growth vessel operating in the anaerobic mode). The resulting mixture of potassium salts is valuable as a de-icer and anti-icer.

The mother liquor from the solids separation step, can be recycled (or partially recycled) to the distillation apparatus via a stream to further enhance recovery of MAS, as well as further convert DAS to MAS.

The solid portion of the cooling-induced crystallization is substantially pure MAS and is, therefore, useful for the known utilities of MAS.

HPLC can be used to detect the presence of nitrogen-containing impurities such as succinamide and succinimide. The purity of MAS can be determined by elemental carbon and nitrogen analysis. An ammonia electrode can be used to determine a crude approximation of MAS purity.

Depending on the circumstances and various operating inputs, there are instances when the fermentation broth may be a clarified MAS-containing fermentation broth or a clarified SA-containing fermentation broth. In those circumstances, it can be advantageous to add MAS, DAS, SA, ammonia and/or ammonium hydroxide to those fermentation broths to facilitate the production of substantially pure MAS. For example, the operating pH of the fermentation broth may be oriented such that the broth is a MAS-containing broth or a SA-containing broth. MAS, DAS, SA, ammonia and/or ammonium hydroxide may be optionally added to those broths to facilitate production of the above-mentioned substantially pure MAS. For example, the operating pH of the fermentation broth may be oriented such that the broth is a MAS-containing broth or a SA-containing broth. MAS, DAS, SA, ammonia, and/or ammonium hydroxide may be optionally added to those broths to attain a broth pH preferably below 6 to facilitate production of the above-mentioned substantially pure MAS. Also, it is possible that MAS, DAS and/or SA from other sources may be added as desired. In one particular form, it is especially advantageous to recycle MAS, DAS and water from the liquid bottoms resulting from the distillation step and/or the liquid portion from the separator into the fermentation broth. In referring to the MAS-containing broth, such broth generally means that the fermentation broth comprises MAS and possibly any number of other components such as DAS and/or SA, whether added and/or produced by bioconversion or otherwise.

The solid portion can be converted into SA by removing ammonia. This can be carried out as follows. The solid portion (consisting essentially of MAS) obtained from any of the above-described conversion processes can be dissolved in water to produce an aqueous MAS solution. This solution can then be distilled at a temperature and pressure sufficient to form an overhead that comprises water and ammonia, and a bottoms that comprises a major portion of SA, a minor portion of MAS and water. The bottoms can be cooled to cause it to separate into a liquid portion in contact with a solid portion that consists essentially of SA and is substantially free of MAS. The solid portion can be separated from the second liquid portion and recovered as substantially pure SA as determined by HPLC.

Figure 2:
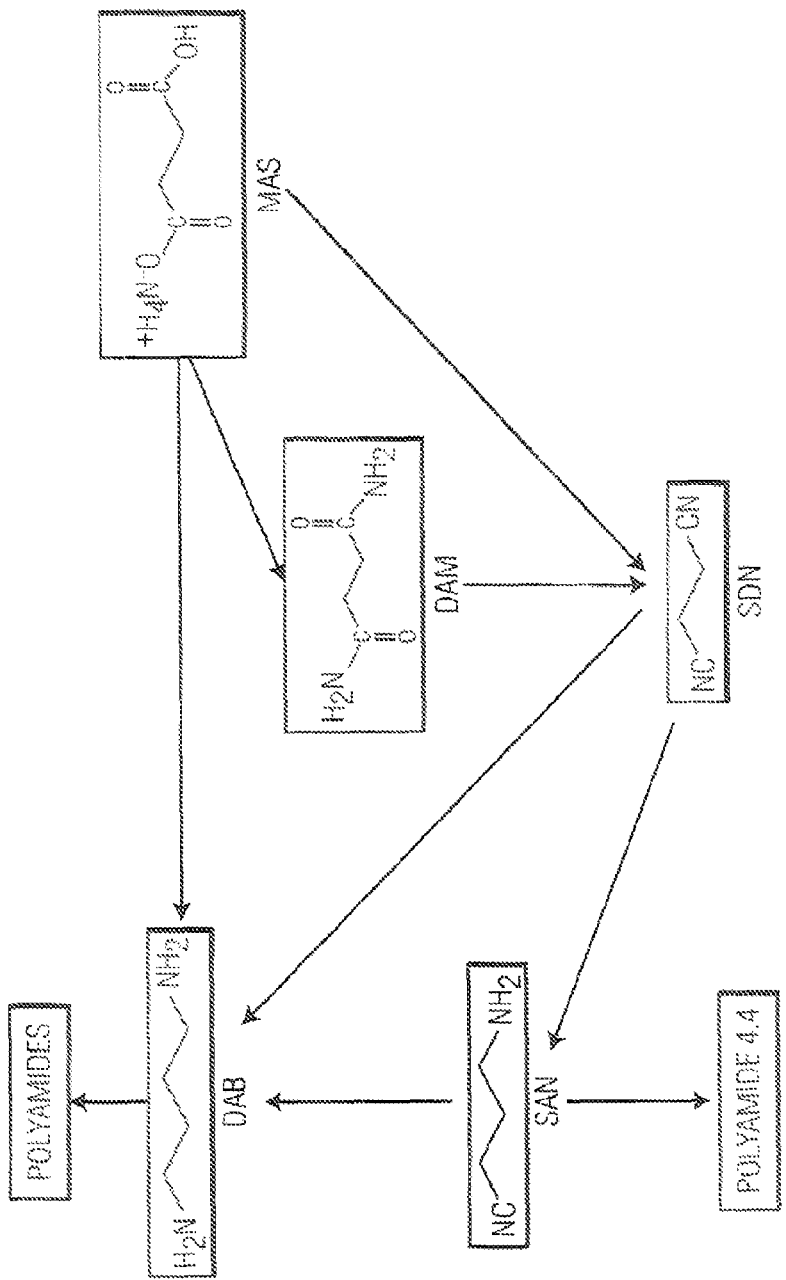
FIG. 2 schematically illustrates various pathways of converting MAS to DAB, SDN and DAM, as well as other intermediates and derivatives.
Figure 3:
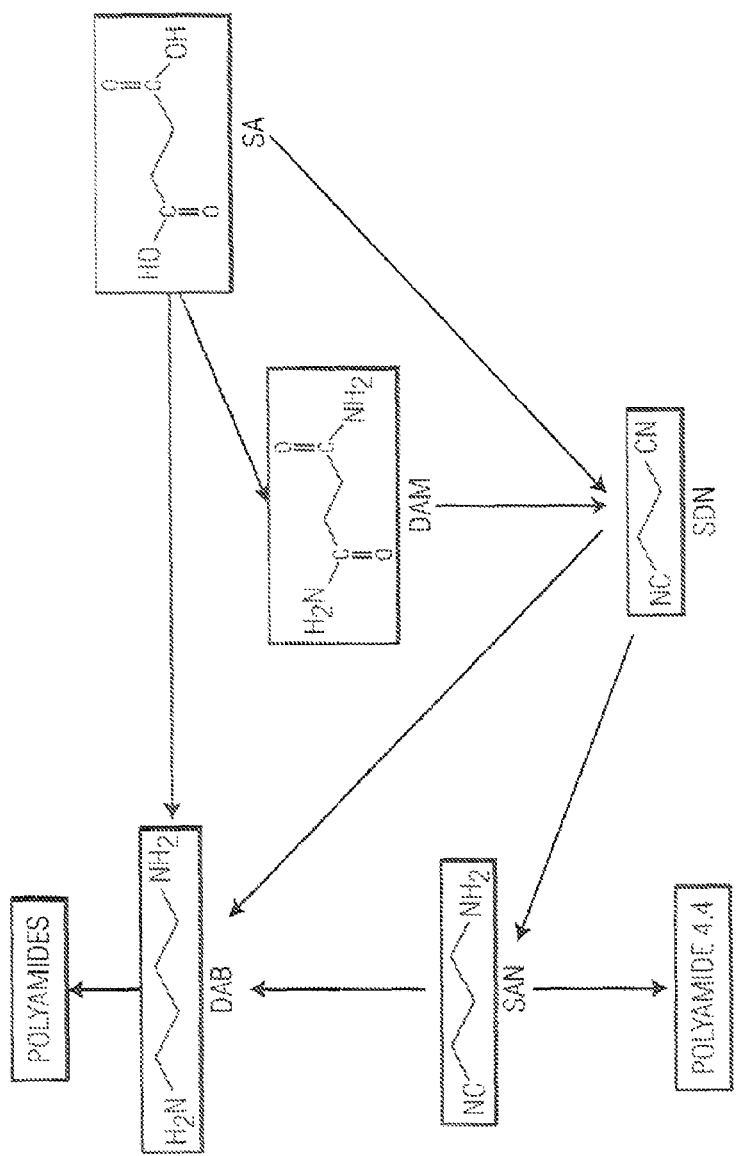
FIG. 3 schematically illustrates various pathways of converting SA to DAB, SDN and DAM, as well as other intermediates and derivatives.

Streams comprising SA, MAS and/or DAS as described above may be converted to selected downstream products such as nitrogen containing compounds including but not limited to DAB, SDN, DAM and the like as described below and illustrated in FIG. 2 and FIG. 3. In initiating those processes, typically the SA, MAS and/or DAS may be dissolved in water to form an aqueous solution thereof which can be directly fed to the downstream reactor.

The SA, MAS or DAS may be converted to SDN directly or indirectly through the intermediate DAM by dehydration. Such dehydrations may be achieved thermally, enzymatically or in the presence of catalysts. Thus, appropriate temperatures, pressures and catalysts are selected to achieve the appropriate level of dehydration, depending on whether the conversion to SDN occurs directly or indirectly.

For example, the conversion can employ an appropriate dehydrating catalyst such as acidic or basic catalysts, including phosphates as disclosed in U.S. Pat. No. 4,237,067 and supported catalysts utilizing Ti, V, Hf or Zr on clays or alumina as disclosed is U.S. Pat. No. 5,587,498. Such catalysts are typically employed at temperatures of 220° C. to 350° C. at pressures of 170-600 psig, for example.

Alternatively, dehydration can be achieved thermally as disclosed in U.S. Pat. No. 3,296,303, wherein acids plus an ammonia source are thermally dehydrated in the presence of glycol solvents at temperatures of 100° C. to 130° C. at pressures of 150 to 200 psig.

As a consequence, SA, MAS or DAS may be dehydrated directly to SDN or indirectly to SDN by the intermediate DAM. Then, once SDN is produced, it is possible to convert SDN directly to an amine such as DAB or to indirectly convert SDN to DAB through the intermediate SAN.

For example, direct conversion from SDN to DAB can be achieved in any number of ways such as disclosed in U.S. Pat. No. 6,376,714, wherein dinitriles in the presence of hydrogen and an ammonia source are converted utilizing catalysts such as Fe, Co, Ni, Rh or Pd promoted with Ru, Cr or W at temperatures of 50° C. to 150° C. at 300 to 1500 psig. The result is high yields of the diamine, in this case DAB.

Similarly, U.S. Pat. No. 4,003,933 converts nitriles to amines with hydrogen over a Co/$ZrO_2$ catalyst at 120° C. to 130° C. and at 1500 psig. Other catalysts may include Fe, Rh, Ir and Pt on $TiO_2$ or $ZrO_2$.

The indirect conversion of SDN to SAN can be achieved by selecting appropriate hydrogenation conditions such as those disclosed in U.S. Pat. No. 5,151,543, wherein nitriles are converted to amino nitriles, in this case SDN to SAN, utilizing RANEY catalysts such as Co or Ni promoted with Fe, Cr or Mo with hydrogen and an ammonia source at 50° C. to 80° C. at pressures of 250 to 1000 psig.

Similarly, the amino nitrile or diamino compounds can be co-produced from dinitriles such as those disclosed in U.S. Pat. No. 7,132,562. U.S. '562 utilizes Fe, Co, Ru, Ni catalysts modified with Cr, V, Ti or Mn at temperatures of 50° C. to 250° C. and 3000 to 5000 psig to achieve high yields and selectivity to the diamine or amino nitrile. The catalysts may also be modified with ordinary P or N with HCN, or CO and hydrogen and an ammonia source.

It is also possible to convert SA, MAS or DAS directly to diamines such as DAB directly or indirectly through DAM. For example, U.S. Pat. No. 2,223,303 discloses the conversion of acids to amines with hydrogen and an ammonia source or alkyl amines with a Cd or Cu catalyst at temperatures of 200° C. to 450° C. at pressures of 10 to 300 ATM. Similarly, U.S. Pat. No. 3,579,583 discloses the conversion of dicarboxylic acids to amines, particularly alkyl amines, utilizing hydrogen and an ammonia source at temperatures of 200° C. to 300° C. at pressures of 100-300 ATM in the presence of a Zn—$Al_2O_3$ or Zn—Cr catalyst.

Further, U.S. Pat. No. 4,935,546 discloses the conversion of acids to amines with hydrogen and an ammonia source in the presence of a Co, Cu or Cr catalyst on a $TiO_2$ or $Al_2O_3$ support at temperatures of 250° C. to 350° C. and at pressures of 20 to 150 bar.

Once the conversions to DAB and SAN have been completed, it is also possible to convert those compounds into polyamide-type compounds in any number of ways known in the art. Representative examples include the following conversions. Polyamides may be produced from amino nitriles such as SAN. One example of conversions of this type may be found in U.S. Pat. No. 5,109,104 which converts an omega amino nitrile in the presence of an oxygenated phosphorus catalyst with water. This is generally achieved in a several-step conversion at temperatures of 200° C. to 330° C. and at pressures ranging from 250 to 350 psig.

An alternative methodology is disclosed in U.S. Pat. No. 6,958,381, wherein a starting monomer such as SAN may be polymerized into a polyamide in the presence of a chain regulator containing a nitrile group and a functional group capable of forming a carboxamide group.

Polyamides may also be formed from the diamines such as DAB, wherein the DAB is polymerized with a dicarboxylic acid or ester to form the polyamide. The preferred dicarboxylic acids have a chain length of $C_4$ to $C_{12}$. The dicarboxylic acid or ester may be an aromatic dicarboxylic acid or ester or it may be an alkyl dicarboxylic acid.

The subject matter and contents of the above-mentioned U.S. Pat. Nos. 4,237,067; 5,587,498; 3,296,303; 6,376,714;

4,003,933; 5,151,543; 7,132,562; 2,223,303; 3,579,583; 4,935,546; 5,109,104; and 6,958,381 are incorporated herein by reference.

EXAMPLES

Our processes are illustrated by the following non-limiting representative examples. In a number of the examples, a synthetic, aqueous DAS solution was used in place of an actual clarified DAS-containing fermentation broth. Other examples use an actual clarified DAS-containing fermentation broth.

The use of a synthetic DAS solution is believed to be a good model for the behavior of an actual broth in our processes because of the solubility of the typical fermentation by-products found in actual broth. The major by-products produced during fermentation are ammonium acetate, ammonium lactate and ammonium formate. If these impurities are present during the distillation step, one would not expect them to lose ammonia and form free acids in significant quantities until all of the DAS had been converted to MAS. This is because acetic acid, lactic acid and formic acid are stronger acids than the second acid group of SA (pKa=5.48). In other words, acetate, lactate, formate and even monohydrogen succinate are weaker bases than the dianion succinate. Furthermore, ammonium acetate, ammonium lactate and ammonium formate are significantly more soluble in water than MAS, and each is typically present in the broth at less than 10% of the DAS concentration. In addition, even if the acids (acetic, formic and lactic acids) were formed during the distillation step, they are miscible with water and will not crystallize from water. This means that the MAS reaches saturation and crystallizes from solution (i.e., forming the solid portion), leaving the acid impurities dissolved in the mother liquor (i.e., the liquid portion).

Example 1

This example demonstrates conversion of a portion of DAS into MAS via distillation and recovery of MAS solids from distillation bottoms liquid via cooling-induced crystallization.

A three neck 500 mL round bottom flask was fitted with a thermometer and Dean Stark trap topped with a reflux condenser. The vent from the reflux condenser went to a scrubbing bottle which contained 100 g of a 1.4M acetic acid solution. The flask was charged with 400 g of a 10% DAS aqueous solution (pH 8.5). The contents of the flask were stirred with a magnetic stirrer and heated with a heating mantle to distill off 320.6 g of distillate (an aqueous ammonia solution) which was removed via the Dean Stark trap. Analysis of the distillate indicated that about 20% of the contained ammonia had been removed from the charged DAS during distillation (i.e., the salts in the bottoms liquid were about 40% MAS and about 60% DAS). Only traces of ammonia were found in the scrubbing bottle. The final temperature of the pot as the last drop distilled over was 110° C. The residue (bottoms liquid) in the pot (73.4 g which was about 53% water) was placed in a flask and allowed to cool to room temperature overnight. Upon cooling to room temperature, white needles of MAS were formed. The white solids were separated via vacuum filtration, yielding 14 g of wet crystals (solid portion) and 56 g of mother liquor (liquid portion). A portion of the wet crystals (7 g) was dried overnight in a vacuum oven, yielding 6 g of dried solids which contained 0.4% water as determined by Karl-Fisher analysis. Analysis of the solids portion with HPLC revealed that the solids portion was free of non-MAS nitrogen-containing impurities (e.g., succinimide and succinamide).

Example 2

This example demonstrates mother liquor recycle.

A 1-L round bottom flask was charged with 800 g of a synthetic 4.5% DAS solution, and then a distillation head was attached to the flask. The contents of the flask were distilled at atmospheric pressure leaving 67 g of residue (bottoms liquid) in the flask. The bottoms liquid contained approximately 45% water. Ammonia analyses of the distillates indicate that the first distillation cycle removed about 29% of the ammonia, making a 42/58 mol/mol mixture of DAS and MAS. The residue (bottoms liquid) was then removed from the flask and placed in a beaker equipped with a water bath. The beaker contents were cooled to 20° C. with stirring. Once the residue reached 20° C., it was seeded with a few crystals of MAS and allowed to stir for 30 minutes. The temperature of the bath was then lowered to 15° C. and held for 30 minutes. The temperature was then lowered to 10° C. and held for 30 minutes. The temperature was then cooled to 5° C. and held for 30 minutes and finally to 0° C. where it was held for 30 minutes. The slurry (consisting of solid and liquid portions) was then quickly filtered using a pre-cooled sintered glass filter funnel and vacuum flask. The solids were dried in a vacuum oven yielding 13.9 g of dry MAS solids. The mother liquor (liquid portion, 47.2 g) was then combined with 800 g of synthetic 4.5% DAS solution and distilled, leaving 86.6 g of residue (bottoms liquid). In the second distillation (i.e., mother liquor recycle run) about 28% of the ammonia from the total amount of DAS present was removed. The residue (bottoms liquid) was then cooled (crystallized) in a similar manner. However, the solution became cloudy at 46° C., so it was seeded at 46° C. and allowed to slowly cool to room temperature overnight while stirring. The next day the temperature was slowly ramped down by 5° C. increments to 0° C. The slurry (solid and liquid portions) was filtered as before, and the solids dried, yielding 23.5 g of MAS solids. This is equal to about a 75% recovery of the SA equivalents in the 800 g of fresh DAS solution distilled. The recovered solids from the first cycle were 95% MAS (about 5% water). In the second cycle, the solids were 97% MAS (about 3% water). The mother liquor from the second cycle contained 28.8% SA equivalents (i.e., as SA salts).

Example 3

This example demonstrates the absence of amide and imide species in the solid portion of cooled distillation bottoms.

A 1-L round bottom flask was charged with 800 g of a synthetic 4.5% DAS solution. The flask was fitted with a five tray 1" Oldershaw section which was capped with a distillation head. The distillate was collected in an ice cooled receiver. The contents of the flask were heated with a heating mantel and stirred with a magnetic stirrer. The contents of the flask were distilled giving 721.1 g of an overhead distillate and 72.2 g of a liquid residue in the flask (i.e. distillation bottoms). The aqueous ammonia distillate was titrated revealing a 0.34% ammonia content (i.e., about 55% conversion of DAS to MAS). The hot distillation bottoms (approximately 47% salt solution of DAS and MAS) were then placed in a 125 mL Erlenmeyer flask and allowed to cool slowly to room temperature while stirring over night. The next morning the cloudy solution was cooled to 15° C. and held for 60 minutes, then cooled to 10° C. and held for 60 minutes and finally cooled to 5° C. and held for 60 minutes while stirring. The resulting white slurry was filtered yielding 12.9 g of wet crystals and 55.3 g of mother liquor. The crystals were dissolved in 25.8 g of distilled water. HPLC analysis of the crystal solution revealed no detectable amounts of amide or imide species. However, HPLC analysis of the mother liquor revealed a trace of succinamic acid, but no detectable succinamide or succinimide.

Example 4

This example produces a solid portion of a cooled distillation bottoms that consists essentially of MAS and is substantially free of DAS.

A three neck 1-L round bottom flask was fitted with an addition funnel and a 1" five tray Oldershaw column which was capped with a distillation head. An ice cooled receiver was used to collect the distillate. The flask was charged with 800 g of a synthetic 4.5% DAS solution. The contents of the flask were heated with a heating mantel and stirred with a magnetic stirrer. Distillation was started. While the distillation occurred an additional 1600 g of the 4.5% DAS solution was slowly added to the flask at the same rate as distillate was taken. A total of 2135 g of distillate was taken overhead. Titration of the distillate revealed the overhead was a 0.33% ammonia solution. The hot aqueous distillation bottoms (253.8 g) was removed from the flask and placed in an Erlenmeyer flask. The distillation bottoms were allowed to slowly cool to room temperature while stirring overnight. The contents of the flask were seeded and allowed to stir for 30 minutes. The slurry was then cooled to 15° C. and held for 60 minutes, then 10° C. and held for 60 minutes and finally to 5° C. and held for 60 minutes all while stirring. The slurry was filtered cold and the solids (i.e., the solid portion) washed three times with about 20 g portions of a cold (about 5° C.) 20% sodium chloride solution to displace the mother liquor (i.e., the liquid portion). Air was sucked through the cake for several minutes to remove as much liquid as possible. The solids were then dried in a vacuum oven at 75° C. for one hour yielding 7.2 g of white crystals. Carbon and nitrogen analyses of the solids revealed a 4.06 atomic ratio of carbon to nitrogen (i.e., a 1.01 ratio of ammonia to SA or about 99% MAS). That a ratio of 1.00 was not obtained is believed to be attributable to incomplete washing of the solids.

Example 5

This example demonstrates the effect of solvents on ammonia evolution from aqueous DAS. Run 5 is the control experiment where no solvent is present.

The outer necks of a three neck 1-L round bottom flask were fitted with a thermometer and a stopper. The center neck was fitted with a five tray 1" Oldershaw section. The Oldershaw section was topped with a distillation head. An ice cooled 500 mL round bottom flask was used as the receiver for the distillation head. The 1-L round bottom flask was charged with distilled water, the solvent being tested, SA and concentrated ammonium hydroxide solution. The contents were stirred with a magnetic stirrer to dissolve all the solids. After the solids dissolved, the contents were heated with the heating mantle to distill 350 g of distillate. The distillate was collected in the ice cooled 500 mL round bottom flask. The pot temperature was recorded as the last drop of distillate was collected. The pot contents were allowed to cool to room temperature and the weight of the residue and weight of the distillate were recorded. The ammonia content of the distillate was then determined via titration. The results were recorded in Table 1.

TABLE 1

| | Run # | | | | |
|---|---|---|---|---|---|
| | 1 | 2 | 3 | 4 | 5 |
| Name of Acid charged | Succinic | Succinic | Succinic | Succinic | Succinic |
| Wt Acid Charged (g) | 11.81 | 11.79 | 11.8 | 11.79 | 11.8 |
| Moles Acid Charged | 0.1 | 0.1 | 0.1 | 0.1 | 0.1 |
| Wt 28% NH3 Solution Charged (g) | 12.11 | 12.09 | 12.1 | 12.11 | 12.1 |
| Moles NH3 Charged | 0.2 | 0.2 | 0.2 | 0.2 | 0.2 |
| Name of Solvent | Diglyme | PG* | GBL** | butoxy triglycol | none |
| Wt Solvent Charged (g) | 400 | 400.1 | 400 | 400 | 0 |
| Wt Water Charged (g) | 400 | 400 | 400 | 400 | 800 |
| Wt Distillate (g) | 350.5 | 351.6 | 350.1 | 350.7 | 351 |
| Wt Residue (g) | 466.3 | 461.7 | 464.3 | 460.9 | 466 |
| % Mass Accountability | 99.1 | 98.7 | 98.9 | 98.5 | 99.2 |
| Wt % NH3 in distillate (titration) | 0.48 | 0.4 | 0.27 | 0.47 | 0.13 |
| Moles NH3 in distillate | 0.099 | 0.083 | 0.056 | 0.097 | 0.027 |
| % NH3 removed in Distillate | 49.5 | 42 | 28 | 49 | 13.4 |
| % First NH3 removed in Distillate | 99 | 84 | 56 | 98 | 27 |
| % Second NH3 removed in Distillate | 0 | 0 | 0 | 0 | 0 |
| Final Pot Temp (° C.) | 101 | 120 | 110 | 107 | 100 |

*PG is propylene glycol
**GBL is gamma butyrolactone

Example 6

This example produced a solid portion from a cooled distillation bottoms that consists essentially of SA and is substantially free of MAS.

A 300 mL Parr autoclave was charged with 80 g of synthetic MAS and 120 g of water. The autoclave was sealed and the contents stirred and heated to about 200° C. at an autogenic pressure of about 190 psig. Once the contents reached temperature, water was fed to the autoclave at a rate of about 2 g/min and vapor removed from the autoclave at a rate of about 2 g/min with a back pressure regulator. Vapor exiting the autoclave was condensed and collected in a receiver. The autoclave was run under these conditions until a total of 1020 g of water had been fed and a total of 1019 g of distillate collected. The distillate was titrated for ammonia content (0.29% ammonia by weight). This translates into an about 29% conversion of MAS to SA. The contents of the autoclave (194.6 g) were partially cooled and discharged from the reactor. The slurry was allowed to stand under stirring at room temperature over night in an Erlenmeyer flask. The slurry was then filtered and the solids rinsed with 25 g of water. The moist solids were dried in a vacuum oven at 75° C. for 1 hr yielding 9.5 g of SA product. Analysis via an ammonium ion electrode revealed 0.013 mmole ammonium ion/g of solid. HPLC analysis revealed the solids were SA with 0.8% succinamic acid impurity.

Example 7

This example used DAS-containing clarified fermentation broth derived from a fermentation broth containing *E. Coli* strain ATCC PTA-5132. This example produced a solid portion of a cooled distillation bottoms that consists essentially of MAS and is substantially free of DAS.

A three neck 1-L round bottom flask was fitted with an addition funnel and a 1" five tray Oldershaw column which was capped with a distillation head. An ice cooled receiver was used to collect the distillate. The flask was charged with 800 g of clarified DAS-containing fermentation broth which contained 4.4% DAS, 1% ammonium acetate, 0.05% ammonium formate and 0.03% ammonium lactate. The contents of the flask were heated with a heating mantel and stirred with a magnetic stirrer. Distillation was started. While the distillation ran, an additional 2200 g of the broth solution was slowly added to the flask at the same rate as distillate was removed. A total of 2703 g of distillate was taken as overhead. Titration of the distillate revealed the overhead was a 0.28% ammonia solution. The hot aqueous distillation bottoms solution (269.7 g) was removed from the flask and placed in an Erlenmeyer flask. The distillation bottoms were allowed to slowly cool to room temperature while stirring overnight. The next day, the contents of the flask were seeded and allowed to stir for 30 minutes. The slurry was then cooled to 15° C. and held for 30 minutes, then to 10° C. and held for 30 minutes and finally to 5° C. and held for 30 minutes, all while stirring. The slurry was filtered cold and air was sucked through the cake for several minutes to remove as much liquid as possible. Light brown solids (72.5 g) and dark brown mother liquor (188.4 g with a pH of 6.4) were obtained. The solids were recrystallized to remove the mother liquor by dissolution in 72 g of water at 50° C. The solution was then allowed to slowly cool to room temperature while stirring overnight. The next day the contents of the flask were seeded and stirred for 30 minutes. The slurry was then cooled to 15° C. and held for 30 minutes, then to 10° C. and held for 30 minutes, and finally to 5° C. and held for 30 minutes, all while stirring. The slurry was filtered cold and air was sucked through the cake for several minutes to remove as much liquid as possible, yielding 110 g of brown mother liquor (pH 5.0). The solids were then dried in a vacuum oven at 75° C. for one hour yielding 24 g of off-white crystals. Carbon and nitrogen analyses of the solids revealed a 4.04 molar ratio of carbon to nitrogen (i.e. a 1.01 ratio of ammonia to SA or about 99% MAS). HPLC analysis revealed that the MAS contained 0.07% succinamic acid but no detectable succinamide, succinimide or acetate species. In other words, the MAS was free of DAS and otherwise substantially pure.

Example 8

This example used fermentation derived MAS from a fermentation broth containing *E. Coli* strain ATCC PTA-5132. This example produced a solid portion from a cooled distillation bottoms that consists essentially of SA and is substantially free of MAS.

A 300 mL Parr autoclave was charged with 80 g of broth derived MAS and 120 g of water. The autoclave was sealed and the contents stirred and heated to about 202° C. at an autogenic pressure of about 205 psig. Once the contents reached temperature, water was fed to the autoclave at a rate of about 2 g/min and vapor was removed from the autoclave at a rate of about 2 g/min with a back pressure regulator. Vapor exiting the autoclave was condensed and collected in a receiver. The autoclave was run under these conditions until a total of 905 g of water had been fed and a total of 908 g of distillate collected. The distillate was titrated for ammonia content (0.38% ammonia by weight). This translates into an about 34% conversion of MAS to SA. The contents of the autoclave (178.2 g) were partially cooled and discharged from the reactor. The slurry was allowed to stand under stirring at room temperature over night in an Erlenmeyer flask. The slurry was then filtered and the solids rinsed with 25 g of water. The moist solids were dried in a vacuum oven at 75° C. for 1 hr yielding 8.5 g of SA product. Analysis via an ammonium ion electrode revealed 0.027 mmole ammonium ion/g of solid. HPLC analysis revealed the solids were SA with 1.4% succinamic acid and 0.1% succinamide impurities.

Example 9

This example used an ammonia releasing solvent to aid deammoniation. This example produced a solid portion from a cooled distillation bottoms that consists essentially of SA and is substantially free of MAS.

A 500 mL round bottom flask was charged with 29 g of MAS solids, 51 g of water and 80 g of triglyme. The flask was fitted with a 5 tray 1" glass Oldershaw column section which was topped with a distillation head. An addition funnel containing 2500 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 2491 g of distillate was taken. The distillate contained 2.3 g of ammonia, as determined by titration. This means about 63% of the MAS was converted to SA. The residue in the flask was then placed in an Erlenmeyer flask and cooled to −5° C. while stirring. After stirring for 30 minutes the slurry was filtered while cold yielding 15.3 g of solids. The solids were dissolved in 15.3 g of hot water and then cooled in an ice bath while stirring. The cold slurry was filtered and the solids dried in a vacuum oven at 100° C. for 2 hrs yielding 6.5 g of succinic acid. HPLC analysis indicated that the solids were SA with 0.18% succinamic acid present.

Example 10

This example used an ammonia releasing solvent to aid deammoniation. This example produced a solid portion of a cooled distillation bottoms that consists essentially of MAS and is substantially free of DAS.

A 500 mL round bottom flask was charged with 80 g of an aqueous 36% DAS solution and 80 g of triglyme. The flask was fitted with a 5 tray 1" glass Oldershaw column section which was topped with a distillation head. An addition funnel containing 700 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 747 g of distillate was taken. The distillate contained 3.7 g of ammonia, as determined by titration. This means about 57% of the ammonia was removed. In other words, all of the DAS was converted into MAS and about 14% of the MAS was further converted into SA. The residue in the flask was then placed in an Erlenmeyer flask and cooled to 5° C. while stirring. After stirring for 30 minutes the slurry was filtered while cold and the solids dried in a vacuum oven at 100° C. for 2 hrs yielding 10.3 g of MAS. Analysis indicated that the solids were MAS with 0.77% succinamic acid and 0.14% succinimide present.

Example 11

This example demonstrates the use of an azeotroping solvent, particularly separation of MAS from other by-products in the broth.

A three neck 500 mL round bottom flask was fitted with a thermometer, a 250 mL addition funnel and a Dean Stark trap topped with a reflux condenser. The flask was charged with 100 g of toluene and 100 g of an about 9% DAS broth solution (which also contained about 1% ammonium acetate and ammonium formate combined). The addition funnel was charged with 250 g of the 9% diammonim succinate broth solution. The contents of the flask were stirred with a magnetic stirrer and heated with a heating mantel bringing the contents to boil. The contents of the addition funnel were added slowly to the flask allowing the toluene-water azeotope to distill into the Dean-Stark trap with return of the toluene to the flask. After all the contents of the addition funnel had been added (at a rate substantially equal to the distillate) the contents were allowed to further reflux until a total of 277.5 g of aqueous phase had been collected from the Dean Stark trap. The contents of the flask were removed while hot and the two phases separated in a warm separatory funnel. The aqueous phase was cooled in an ice bath while being stirred. The resulting solids were recovered via filtration using a sintered glass funnel. The mother liquor was dark brown and the filtered solids were off-white. The solids were dried in a vacuum oven and analyzed via HPLC. The dried solids (5.7 g) were about 96% monoammonium succinate and about 1% ammonium acetate with the rest being water.

Example 12

A pressure distillation column was constructed using an 8 ft long 1.5" 316 SS Schedule 40 pipe packed with 316 SS Propak packing. The base of the column was equipped with an immersion heater to serve as the reboiler. Nitrogen was injected into the reboiler via a needle valve to pressure. The overhead of the column had a total take-off line which went to a 316 SS shell and tube condenser with a receiver. The receiver was equipped with a pressure gauge and a back pressure regulator. Material was removed from the overhead receiver via blowcasing through a needle valve. Preheated feed was injected into the column at the top of the packing via a pump. Preheated water was also injected into the reboiler via a pump. This column was operated at 30 psig pressure which gave a column temperature of 137° C. The top of the column was fed a synthetic 10% DAS solution at a rate of 5 mL/min and water was fed to the reboiler at a rate of 5 mL/min. The overhead distillate rate was 8 mL/min and the residue rate was 2 mL/min. Titration of the distillate for ammonia indicated that the about 47% of the ammonia had been removed in the distillate (i.e. the conversion to MAS was about 94%). The residue liquid was about 20% MAS and HPLC analysis of the residue indicated an about 3% inefficiency to succinamic acid.

Example 13

A portion of the residue (800 g) from Example 12 was concentrated via a batch distillation to about 59% MAS solution (i.e. 530 g of water was distilled off). The residue was then cooled to 5° C. while stirring. The resulting slurry was filtered and the solids dried in a vacuum oven at 75° C. for 1 hour yielding 52.5 g of MAS solids (i.e. about 32% recovery). HPLC analysis indicated that the solids contained 0.49% succinamic acid and no succinimide.

Example 14

A second portion of the pressure column residue (3200 g) from Example 12 was placed in the evaporative crystallizer and concentrated to about 72% MAS by distilling off 2312 g of water at 60° C. under vacuum. The resulting hot slurry was centrifuged and the recovered solids dried in the vacuum oven at 75° C. for one hour yielding 130.7 g of MAS solids. The mother liquor from the centrifuging step was allowed to cool to room temperature forming a second crop of crystals. This slurry was filtered and the recovered solids were dried at 75° C. under vacuum yielding 114.8 g of MAS solids. Based on the succinate concentration of the feed to the crystallizer, a 20% and 18% recovery was realized for the first and second crops, respectively (i.e. a 38% overall recovery). HPLC analysis of the two crops of solids indicated that the first crop had no detectable succinamic acid and succinimide while the second crop had 0.96% succinamic acid and 0.28% succinimide.

Comparative Example 1

This example demonstrates that an atmospheric distillation of an aqueous MAS solution removes very little ammonia when triglyme is not present.

A 500 mL round bottom flask was charged with 30 g of MAS solids and 120 g of water. The flask was fitted with a 5 tray 1" glass Oldershaw column section which was topped with a distillation head. An addition funnel containing 600 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 606 g of distillate was taken. The distillate contained 0.15 g of ammonia, as determined by titration. This means ~4% of the MAS was converted to SA.

Comparative Example 2

This example demonstrates the decrease in ammonia removal for DAS when triglyme is not present.

A 500 mL round bottom flask was charged with 80 g of an aqueous 36% DAS solution and 80 g of water. The flask was fitted with a 5 tray 1" glass Oldershaw column section which was topped with a distillation head. An addition funnel containing 1200 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 1290 g of distillate was taken. The distillate contained 2.2 g of ammonia, as determined by titration. This means about 44% of the DAS was converted to MAS.

Although our processes have been described in connection with specific steps and forms thereof, it will be appreciated that a wide variety of equivalents may be substituted for the specified elements and steps described herein without departing from the spirit and scope of this disclosure as described in the appended claims.

The invention claimed is:

1. A process for making nitrogen containing compounds, comprising:
    (a) providing a clarified DAS-containing fermentation broth;
    (b) distilling the broth to form an overhead that comprises water and ammonia, and a liquid bottoms that comprises MAS, at least some DAS, and at least about 20 wt % water;
    (c) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS;
    (d) separating at least part of the solid portion from the liquid portion;
    (e) (1) contacting the solid portion with hydrogen and optionally an ammonia source in the presence of at least one hydrogenation catalyst to produce DAB; or
        (2) dehydrating at least a part of the solid portion to produce SDN; or
        (3) dehydrating at least a part of the solid portion to produce DAM; and
    (f) recovering the DAB, SDN or DAM.

2. A process for making nitrogen containing compounds, comprising:
    (a) providing a clarified DAS-containing fermentation broth;
    (b) distilling the broth to form a first overhead that includes water and ammonia, and a first liquid bottoms that includes MAS, at least some DAS, and at least about 20 wt % water;
    (c) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS;
    (d) separating the solid portion from the liquid portion;
    (e) recovering the solid portion;
    (f) dissolving the solid portion in water to produce an aqueous MAS solution;
    (g) distilling the aqueous MAS solution at a temperature and pressure sufficient to form a second overhead that includes water and ammonia, and a second bottoms that includes a major portion of SA, a minor portion of MAS, and water;
    (h) cooling and/or evaporating the second bottoms to cause the second bottoms to separate into a second liquid portion in contact with a second solid portion that preferably consists essentially of SA and is substantially free of MAS;
    (i) separating at least part of the second solid portion from the second liquid portion;
    (j) (1) contacting the second solid portion with hydrogen and an ammonia source in the presence of at least one hydrogenation catalyst to produce DAB; or
        (2) dehydrating at least a part of the second solid portion to produce SDN; or
        (3) dehydrating at least a part of the second solid portion to produce DAM; and
    (k) recovering the DAB, SDN or DAM.

3. A process for making nitrogen containing compounds, comprising:
    (a) providing a clarified MAS-containing fermentation broth;
    (b) optionally, adding MAS, DAS, SA, $NH_3$, and/or $NH_4^+$ to the broth to preferably maintain the pH of the broth below 6;
    (c) distilling the broth to form an overhead that includes water and optionally ammonia, and a liquid bottoms that includes MAS, at least some DAS, and at least about 20 wt % water;
    (d) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS;
    (e) separating at least part of the solid portion from the liquid portion;
    (f) (1) contacting the solid portion with hydrogen and optionally an ammonia source in the presence of at least one hydrogenation catalyst to produce DAB; or
        (2) dehydrating at least a part of the second solid portion to produce SDN; or
        (3) dehydrating at least a part of the second solid portion to produce DAM; and
    (g) recovering the DAB, SDN or DAM.

4. A process for making nitrogen containing compounds, comprising:
    (a) providing a clarified MAS-containing fermentation broth;
    (b) optionally, adding MAS, DAS, SA, $NH_3$, and/or $NH_4^+$ to the broth to preferably maintain the pH of the broth below 6;
    (c) distilling the broth to form an overhead that includes water and optionally ammonia, and a liquid bottoms that includes MAS, at least some DAS, and at least about 20 wt % water;
    (d) cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS;
    (e) separating the solid portion from the liquid portion; and
    (f) recovering the solid portion;
    (g) dissolving the solid portion in water to produce an aqueous MAS solution;
    (h) distilling the aqueous MAS solution at a temperature and pressure sufficient to form a second overhead that includes water and ammonia, and a second bottoms that includes a major portion of SA, a minor portion of MAS, and water;
    (i) cooling and/or evaporating the second bottoms to cause the second bottoms to separate into a second liquid portion in contact with a second solid portion that preferably consists essentially of SA and is substantially free of MAS;
    (j) separating at least part of the second solid portion from the second liquid portion;

(k) (1) contacting the solid portion with hydrogen and an ammonia source in the presence of at least one hydrogenation catalyst to produce DAB; or
(2) dehydrating at least a part of the solid portion to produce SDN; or
(3) dehydrating at least a part of the solid portion to produce DAM; and
(l) recovering the DAB, SDN or DAM.

5. The processes of claim 1, further comprising polymerizing the DAB with a dicarboxylic acid or ester to form a polyamide.

6. The processes of claim 1, further comprising contacting the SDN with hydrogen and ammonia in the presence of a hydrogenation catalyst to produce DAB.

7. The process of claim 6, further comprising polymerizing the DAB with a dicarboxylic acid or ester to form a polyamide.

8. The processes of claim 1, further comprising contacting the SDN with hydrogen and ammonia in the presence of a hydrogenation catalyst to produce a composition comprising SAN.

9. The process of claim 8, further comprising polymerizing the SAN to form a polyamide.

10. The process of claim 8, further comprising contacting the SAN with hydrogen and ammonia in the presence of a hydrogenation catalyst to produce DAB.

11. The process of claim 10, further comprising polymerizing the DAB with a dicarboxylic acid or ester to form a polyamide.

12. The process of claim 1, further comprising dehydrating the DAM to produce SDN.

13. The process of claim 12, further comprising contacting the SDN with hydrogen and ammonia in the presence of a hydrogenation catalyst to produce DAB.

14. The process of claim 13, further comprising polymerizing the DAB with a dicarboxylic acid or ester to form a polyamide.

15. The process of claim 12, further comprising contacting the SDN with hydrogen and ammonia in the presence of a hydrogenation catalyst to produce a composition comprising SAN.

16. The process of claim 15, further comprising polymerizing the SAN to form a polyamide.

17. The process of claim 15, further comprising contacting the SAN with hydrogen and ammonia in the presence of a hydrogenation catalyst to produce DAB.

18. The process of claim 17, further comprising polymerizing the DAB with a dicarboxylic acid or ester to form a polyamide.

19. The processes of claim 1, wherein the distillations are carried out in the presence of an ammonia separating solvent which is at least one selected from the group consisting of diglyme, triglyme, tetraglyme, sulfoxides, amides, sulfones, polyethyleneglycol (PEG), butoxytriglycol, N-methylpyrolidone (NMP), ethers, and methyl ethyl ketone (MEK) or in the presence of a water azeotroping solvent which is at least one selected from the group consisting of toluene, xylene, methylcyclohexane, methyl isobutyl ketone, hexane, cyclohexane and heptane.

\* \* \* \* \*